United States Patent [19]
Chu

[11] Patent Number: 5,330,448
[45] Date of Patent: Jul. 19, 1994

[54] METHOD AND APPARATUS FOR MEDICAL FLUID TRANSFER

[76] Inventor: Cristina Chu, 7 Richard Rd., Lexington, Mass. 02173

[21] Appl. No.: 934,300

[22] Filed: Aug. 24, 1992

Related U.S. Application Data

[63] Continuation of Ser. No. 490,764, Mar. 8, 1990, abandoned.

[51] Int. Cl.$^5$ .............................................. A61M 5/00
[52] U.S. Cl. ...................................... 604/280; 604/86; 604/4; 604/175
[58] Field of Search .................. 604/4, 5, 6, 27, 28, 604/29, 86, 263, 280, 244, 175

[56] References Cited

U.S. PATENT DOCUMENTS

| | | | |
|---|---|---|---|
| 4,184,497 | 1/1980 | Kolff et al. | 604/27 |
| 4,464,178 | 8/1984 | Dalton | 128/DIG. 26 X |
| 4,496,349 | 1/1985 | Consentino | 604/175 |
| 4,585,436 | 4/1986 | Davis et al. | 604/4 X |
| 4,726,381 | 2/1988 | Jones | 128/632 |
| 4,781,693 | 11/1988 | Martinez et al. | 604/244 X |
| 4,810,241 | 3/1989 | Rogers | 604/29 X |
| 4,966,582 | 10/1990 | Sit et al. | 604/86 |

Primary Examiner—Robert A. Hafer
Assistant Examiner—Sam Rimell
Attorney, Agent, or Firm—Wolf, Greenfield & Sacks

[57] ABSTRACT

This invention relates to a method and apparatus for transferring a selected fluid in a selected direction to and from a selected body area of a medical patient. More particularly, this invention involves a surgically implanted catheter which is sealed at its proximal end with a material which may be repeatedly punctured by a needle and which reseals when the needle is removed. A needle attached through tubing to a suitable source or sink of the fluid pierces the seal and is latched thereto by suitable means. A noninvasive pump is provided to maintain a desired flow rate. To enhance seal life, a disposable seal portion may be provided having a needle which pierces the seal at the end of the catheter and is latched thereto and having a seal at its proximal end which may be pierced by the needle attached to the source or sink of fluid. When the seal on the disposable section wears out, this section may be removed and replaced, permitting the seal on the surgically implanted catheter to remain for an extended period of time. Various techniques are also provided for replacing the seal at the end of the catheter if necessary.

15 Claims, 5 Drawing Sheets

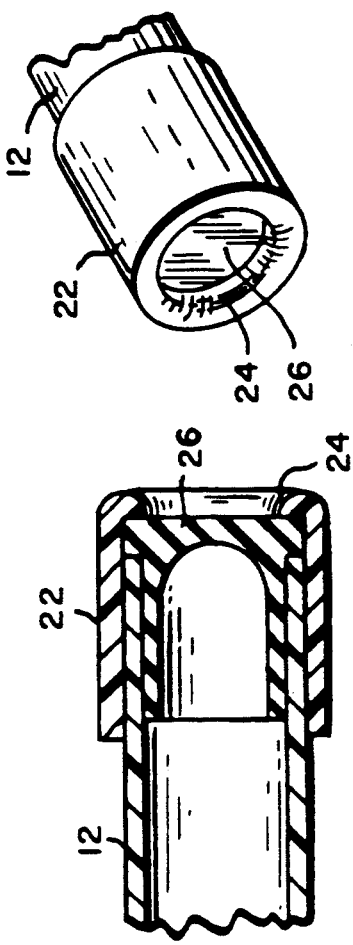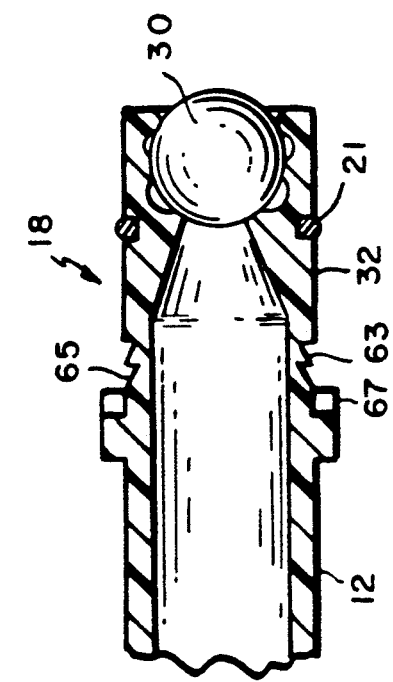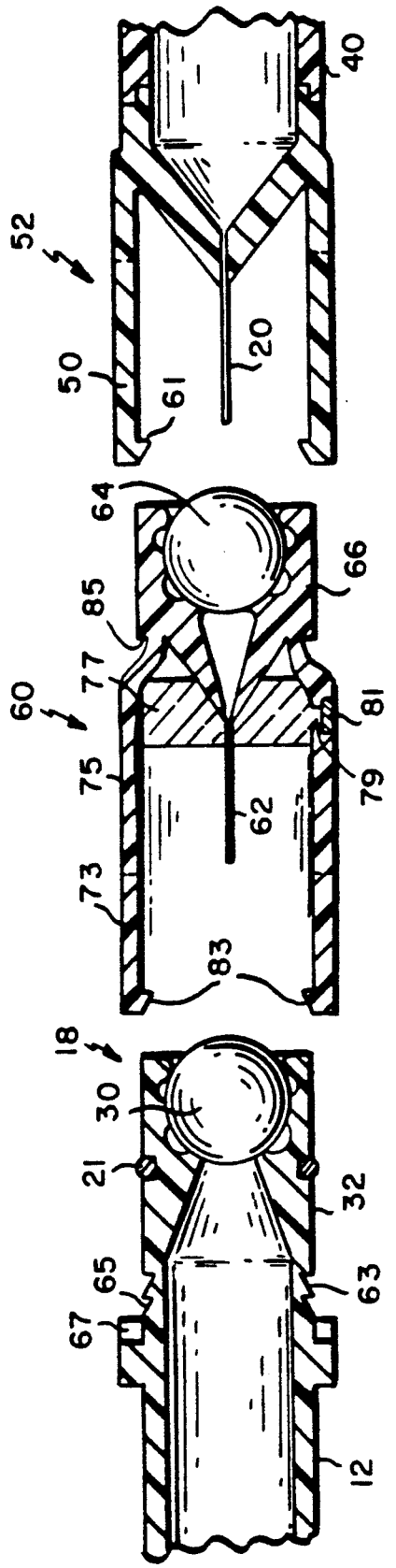

METHOD AND APPARATUS FOR MEDICAL FLUID TRANSFER

This is a continuation of copending application Ser. No. 07/490,764 filed on Mar. 8, 1990, now abandoned.

FIELD OF THE INVENTION

This invention relates to methods and apparatus for transferring a selected fluid in a desired direction to and from a selected body area of a medical patient, and more particularly to such a method and apparatus which utilizes a sealed surgically implanted catheter.

BACKGROUND OF THE INVENTION

There are a number of medical procedures which involve the frequent introduction of a medicinal liquid or biological fluid into a selected body area of a patient or the withdrawal of a medicinal or biological fluid from a patient. While needles can be used for such purposes where the area of the body is close to the surface, for example to inject a fluid into the bloodstream, there are some treatments, such as peritoneal dialysis, where needles cannot reach and it is required to surgically implant a catheter in order to introduce the desired fluid and for the removal thereof. Even for procedures where a needle may be utilized, repeated puncturing of veins with needles results in damage to the veins which makes it difficult to find a suitable site for further punctures. This results in pain and anxiety to the patient, both of which are undesirable. Further, if a needle remains in the patient for an extended period of time, the needle can infiltrate, preventing proper introduction of the substance, causing extreme discomfort to the patient, and possibly leading to infection or other injury to the patient. For these reasons, patients who are going to be receiving frequent medical procedures involving the introduction or withdrawal of fluids, such as cancer patients undergoing chemotherapy, frequently have catheters surgically implanted which may be used for the introduction of the medicinal fluid.

However, surgically implanted catheters are usually open on the proximal end and, while some sort of temporary seal may be put on the catheter when not in use, the catheters basically provide an open channel into the patient's body. As a result, these catheters expose the patient to infection, and even with careful cleaning and sterilization of the ends of these catheters at regular intervals and after use, using various means such as ultraviolet or microwave radiation, the infection rate on patients having such catheters is still relatively high. With cleaning, but without sterilization, an average of sixty percent of patients having such catheters for peritoneal dialysis develop infections during the first year.

The risk of infection with surgically implanted catheters and the time, trouble and expense involved in the frequent cleaning and sterilization of such catheters in order to minimize infection, has resulted in surgically implanted catheters being used only in limited situations, such as peritoneal dialysis, where there is no other feasible way to reach the desired area of the body, or in situations where the condition of the patient's veins makes it nonfeasible to continue treatment by use of needles. However, if a procedure could be developed which would permit such catheters to be permanently sealed, thus minimizing infection, while still permitting medicinal or biologic fluids to be transferred therethrough, such catheters could be used far more extensively, not only for peritoneal dialysis, but for cancer patients undergoing chemotherapy, patients in hospitals requiring frequent introduction of blood or intravenous substances, diabetics requiring regular shots of insulin and the like. Such a procedure would also be highly advantage for peritoneal dialysis patients, cancer patients and others currently having implanted catheters in that the risk of infection could be substantially reduced while the time and expense involved in cleaning and sterilizing the catheters would be virtually eliminated.

One way of solving the above problem is to seal the catheter with a rubber seal as is used on bottles containing an injectable substance or a standard compressible rubber ball seal. A hypodermic needle, which could be either a standard needle or one especially designed for this purpose, could be utilized to pierce the seal and the desired medicinal or biologic fluids could be introduced or withdrawn through the needle. On the withdrawal of the needle, the seal would immediately close behind the needle preventing infection from getting in, and an alcohol wipe could be used over the seal as the needle is withdrawn or just after the needle is withdrawn to further reduce the possibility of infection. The wiping action of the seal on the needle would also tend to clean the needle on introduction to further reduce the possibility of an infectious agent being introduced.

However, there are two potential problems in using such a rubber seal and needle arrangement. First, while such seals may be punctured a substantial number of times before they lose the elasticity to reseal, the number of times the seal may be punctured varying somewhat with the gauge of needle used, to minimize infection it is preferable that the seal not be used to any way near its maximum theoretical number of punctures. Thus, for a seal with a theoretical life of one hundred and eighty punctures, it might be necessary to replace the seal after for example one hundred to one hundred and fifty punctures. Since procedures such as peritoneal dialysis may require as many as four punctures a day, this would mean that a single seal would only last for approximately one month. Since a patient should not be subjected to a surgical procedure, even a relatively simple surgical procedure, on a monthly basis if such can be avoided, it is desirable that the seal either be replaceable without requiring surgical implantation of a new catheter, or that procedures be provided for extending the life of the seal for several years.

The second potential problem is that a reasonably flow rate may be required in order to permit the medical procedure to be completed within an acceptable time period. For example, for peritoneal dialysis, it is required that two liters of dialysate be transferred over a twenty- to thirty-minute time period, requiring a flow rate in the 60–100 ml/min range. Relying on gravity, or other similar means, it may not be possible to achieve the desired flow rate through a standard needle. A means must therefore be provided for enhancing the flow rate of the selected fluid through the needle so that a desired flow rate can be achieved.

A need therefore exists for a method and apparatus for providing a seal for a surgically implanted catheter which seal permits desired fluids to pass therethrough at a required flow rate. Such seal should either be replaceable without requiring surgical procedure or the life of the seal should be extended to a point where surgical reimplantation or replacement of the catheter is not required for several years.

SUMMARY OF THE INVENTION

In accordance with the above, this invention provides a method and apparatus for transferring a selected fluid in a desired direction to or from a selected body area of a medical patient. A catheter is surgically implanted at its distal end in the body area, the proximal end of the catheter extending from the patient's body. The proximal end of the catheter is sealed with a seal of a material which may be repeatedly punctured by a needle and which reseals when the needle is removed. A receptacle means is provided which is adapted to function as a source or sink for the selected fluid and is connected by a suitable tube to a needle which is adapted to puncture the seal. A noninvasive pump may be provided for pumping the selected fluid in the desired direction between the body area and the receptacle.

The seal is preferably a compression rubber seal which may be formed of silicon rubber and is preferably in the form of a spherical piece of rubber which is compression mounted to the catheter end. Either the entire seal or the spherical rubber portion thereof may be removed and replaced. While the seal may be removably mounted to the catheter so that it may be removed and replaced, it is preferable that it be cut off the end of the catheter or that special equipment be required to remove the seal so that it may not be removed by the patient, thus reducing the likelihood of infection.

It is also preferable that relative movement between the needle and the seal be prevented after the needle punctures the seal to minimize damage to the seal, and suitable means should be provided for preventing such relative movement. To prevent the needle from being inadvertently pulled from the seal, it is also preferable that means be provided to latch the two together.

Another way the life of the seal can be increased is to provide a disposable section having a tubular member with a second needle mounted at one end and a second puncturable seal at the other end. The disposable section is mounted with its needle piercing the seal on the catheter and remains in that position for multiple punctures of the disposable section's seal by the needle. After a predetermined number of uses, when the seal on the disposable section starts to deteriorate, the disposable section is removed and the needle of a new disposable section is forced through the catheter seal. Again, it is preferred that special equipment be required to remove the disposable sections to minimize patient tampering and that the disposable sections be rendered unuseable when removed. Thus, a single catheter seal may be utilized for the life of over one hundred disposable sections or in other words well in excess of ten thousand total uses.

The foregoing and other objects, features and advantages of the invention will be apparent from the following more particular description of preferred embodiments of the invention as illustrated in the accompanying drawings.

IN THE DRAWINGS

FIG. 2 is an enlarged cutaway side view of a removable catheter seal in accordance with one embodiment of the invention.

FIGS. 3A and 3B are a cutaway side view and a front perspective view respectively of a catheter seal in accordance with a second embodiment of the invention.

FIG. 4A is a cutaway, exploded or unassembled side view of a tandem seal embodiment of the invention.

DETAILED DESCRIPTION

Figure 1:
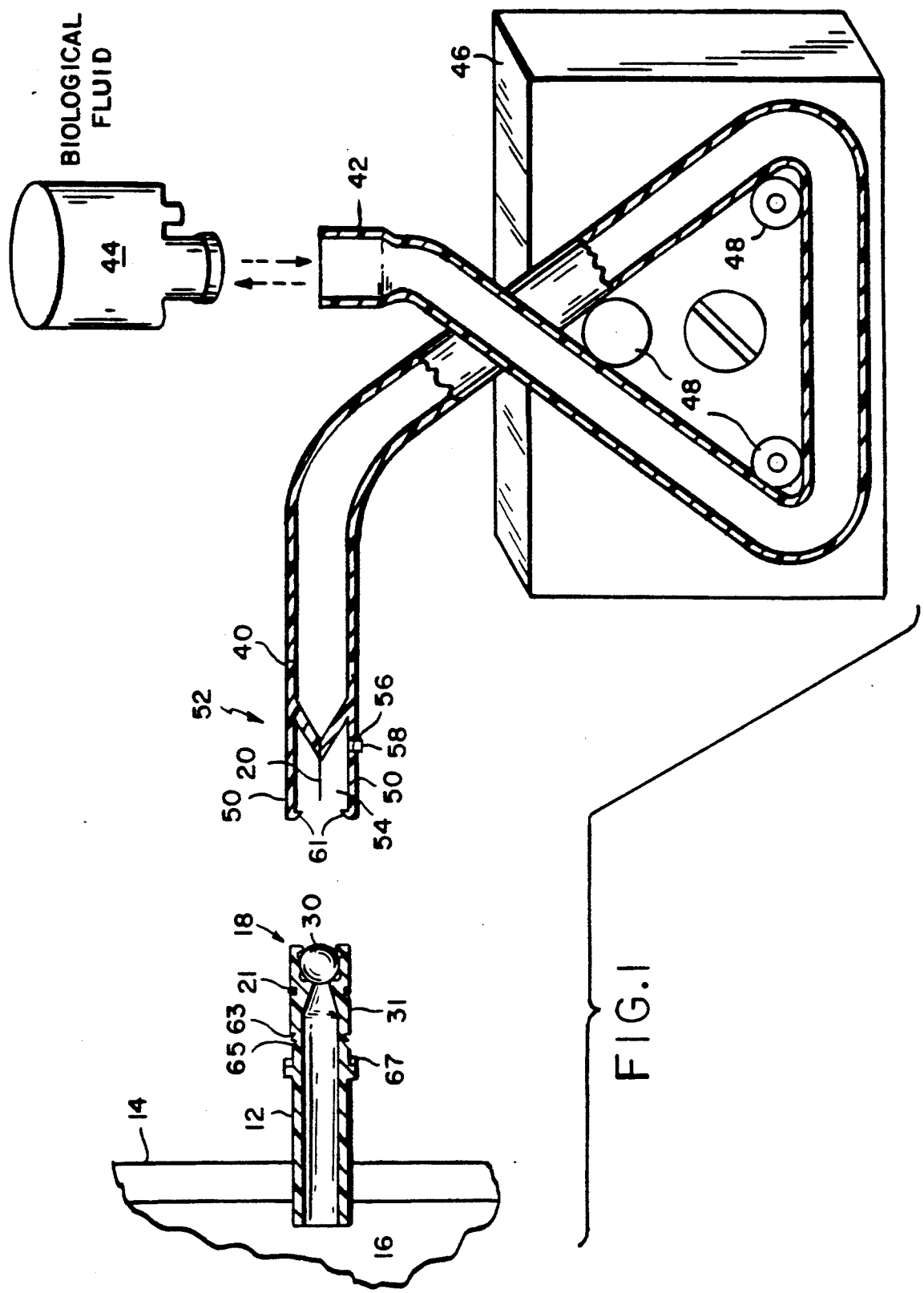
FIG. 1 is a partially diagrammatic, partially cutaway, partially exploded or unassembled side view of an apparatus for transferring a medicinal or biologic fluid in accordance with the teachings of this invention.

FIG. 1 is a somewhat diagrammatic side view of apparatus in accordance with the teachings of this invention which may be utilized to transfer a medicinal, biological, or other fluid in either direction between a selected body area of a patient and a receptacle which may serve as a source or sink for such fluid. In FIG. 1, it is assumed that the apparatus is being used to perform peritoneal dialysis; however, this is by no means a limitation on the invention. In FIG. 1, a catheter 12 has been surgically implanted in the stomach area of a patient 14 adjacent the peritoneal membrane 16. The proximal end of the catheter which extends from the patient has a seal 18 mounted thereon. Seal 18 is designed to prevent dirt, germs, or any other infection-causing agent from passing therethrough into catheter 12, while permitting a needle 20, which may be a standard hypodermic needle, to pass therethrough.

FIGS. 3A and 3B show one type of seal which may be used as the seal 18. This seal, which is the seal used for sealing bottles containing substances which are to be administered to a patient by injection, has a cap 22, which may be of plastic, metal or other suitable material, which is secured to catheter 12 by suitable means, such as gluing, crimping, heat forming or the like. Cap 22 has a circular opening 24 in its proximal end in which is sealed a suitably shaped rubber stopper 26. Stopper 26 may for example be formed of silicon rubber. A needle may gain access to catheter 12 by being passed through opening 24 and the rubber stopper 26 into the catheter. Cap 22 is preferably crimped or otherwise formed onto stopper 26 so as to apply pressure thereto, thereby enhancing the sealing properties of stopper 26 and enhancing the ability of the seal to reclose behind a needle 20 as the needle is withdrawn.

While the seal shown in FIGS. 3A and 3B is relatively inexpensive, it presents a small area through which a needle may be inserted and has a relatively small amount of rubber through which the needle passes. The seal therefore can be utilized for only a limited number of punctures before it is no longer effective as a seal. It is therefore preferable for this application, where it is desired that numerous punctures be possible before there is a need to replace the seal, that a spherical ball seal such as that shown in FIGS. 1 and 2 be utilized as the seal 18. With this seal, a spherical ball 30 of silicon rubber is enclosed under pressure in a housing 32 which is fused in the factory or otherwise suitably secured to the proximal end of catheter 12. The proximal end of ball 30 is exposed so as to be pierceable by needle 20. A sealing O-ring 21 is provided around the periphery of housing 32.

Needle 20 is connected through a flexible section of tubing 40 and a junction 42 to a receptacle 44. Receptacle 44 may for example contain dialysate or other medicinal or biologic fluid to be applied to the individual, or may be a sink which is to receive used dialysate containing various bodily wastes, blood, or other fluid to be withdrawn from the individual. In the case of peritoneal dialysis, receptacle 44 could serve both as a source of clean dialysate and as a receptacle or sink for the used dialysate containing bodily wastes. For the embodiment of the invention shown in FIG. 1, tubing 40 is passed through a standard noninvasive pump 46 which may be operated in one direction to pump fluid into patient 14 and in the opposite direction to cause fluid to be withdrawn from the patient. For the pump shown in FIG. 1, pumping is accomplished by rollers 48 squeezing tubing 40 against the walls of a cylindrical casing.

In use, needle 20 is applied to puncture for example ball 30 of seal 18. An alcohol wipe may be applied over the seal before puncture. If nothing else were done at this point, the needle could move around in the seal, thus enlarging the hole through which the needle passes. The enlarged hole might permit an infectious agent to enter catheter 12, and in any event would adversely affect the life of the seal and the resealing properties of seal 18 when needle 20 is withdrawn. It is also possible that, absent some latching means, the needle could be inadvertently withdrawn from the seal with, in some situations, potentially catastrophic results. It is therefore desirable that the seal 18 and needle 20 be latched together in some way so that there is little if any relative movement between the two when the needle is passed through the seal and the two cannot be inadvertently separated. A number of standard mechanisms can be utilized for accomplishing this function.

Figure 4B:
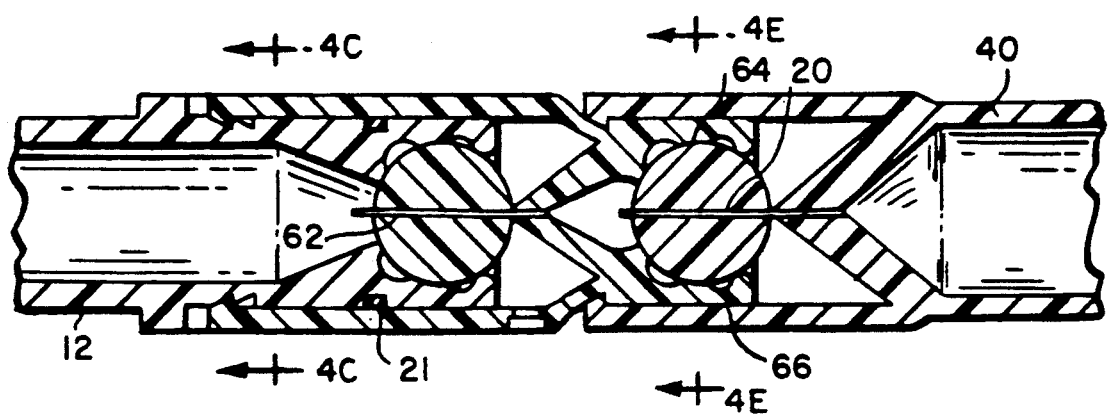
FIG. 4B is a cutaway side view of the tandem seal embodiment of FIG. 4A with the elements thereof assembled.
Figure 4C:
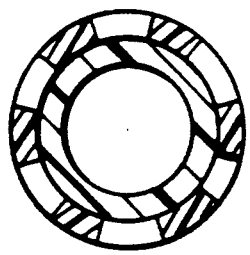
FIG. 4C is a sectional view taken along the line C—C in FIG. 4B.
Figure 4D:
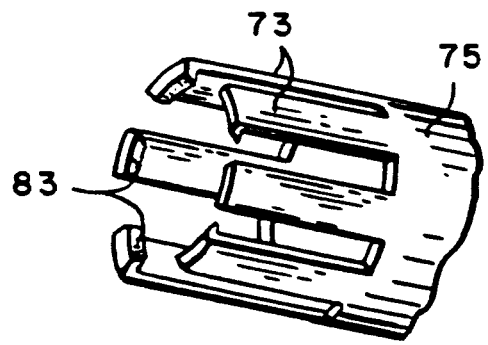
FIG. 4D is a perspective view of gripping fingers useable with the disposable section for the embodiment of the invention shown in FIGS. 4A-4C.
Figure 4E:
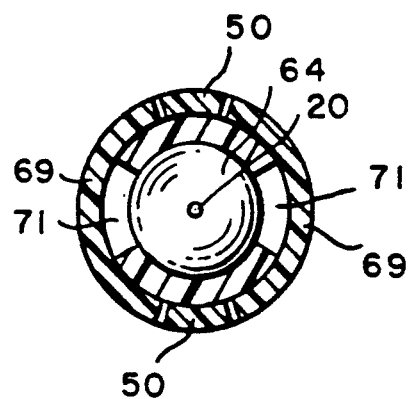
FIG. 4E is a sectional view taken along the line E—E in FIG. 4B.

For the preferred embodiment shown in FIG. 1, this is accomplished by having at least two flexigrip fingers 50 which extend from a cap 52 secured to the end of tube 40 adjacent seal 18. Needle 20 is also mounted in cap 52 and, as will be described in greater detail in connection with the embodiment of FIG. 4, an antiseptic gel may be provided in the shaded region 54 to enhance the sterility of this region. A bleeder hole 56 covered by a rubber 0-ring 58 enables excess gel to be squeezed out during insertion of needle 20 into ball 30 of seal 18, with the O-ring sealing the opening 56 at other times. Each flexigrip finger 52 has a gripping projection 60 with a ramp leading edge at its end. The fingers 60 expand as the ramp leading edge of projections 60 ride up over the forward end of casing 32 of seal 18 and drop into grooves 63 and 65 formed in the rear outer surface of housing 32. When proper pressure is exerted, the projection 61 will nest in groove 65 and will be pressed into engagement in these grooves by the action of O-ring seal 67. Groove 63 is provided as a safety precaution to prevent inadvertent disconnection of the seal. As may be best seen in FIG. 4E, the portion 69 of the forward section of cap 52 which is not taken up with fingers 50 is solid so that the forward end of cap 52 covers a substantial portion of housing 32 when the elements are assembled. This prevents relative movement between the needle and seal, the locking action of projection 61 in groove 65 normally preventing separation of these two elements.

When it is desired to separate needle 20 from seal 18, this may be accomplished in one of two ways. The first way is to push housing 52 slightly toward seal 18 and to press on fingers 50 at approximately the point where O-ring 58 is located. This will push the fingers out of groove 65 and permit the two elements to be separated.

An alternative way is to provide a pair of grooves 71 in housing 32, which grooves are slightly larger than fingers 50. To separate needle 20 from seal 18, cap 52 is rotated relative to housing 32 to align fingers 50 with grooves 71 and the seal and needle may then be pulled apart. Lines or other suitable markings may be provided on housing 32 or on both housings to assist in this process.

The securing together of the cap 52 at the end of tube 40 and seal 18 may also be accomplished by having screw threads on the outside of housing 32 and providing an internally threaded cap on element 52 which permits the two elements to be screwed together. Similar results could be obtained by having a bayonet-type latch with the male portion of the latch mounted on the outside of housing 32 and the female portion of the bayonet coupling on cap 52. Other suitable latching means known in the art might also be utilized.

While the seal 18 may be replaceable so that catheter 12 may be utilized over an extended period of time without requiring surgical replacement, a preferred way of achieving this result is by providing a means for extending the life of seal 18. FIGS. 4A-4E show a tandem seal embodiment for accomplishing this objective, which embodiment is the preferred embodiment of the invention.

For this embodiment, a disposable or tandem section 60 is provided which consists of a needle 62 and a seal 64 which are contained within a short tubular housing 66. Needle 62 will be the same as needle 20 and seal 64 may be substantially identical to seal 18. The forward end of housing 66 has a plurality of flexgrip fingers 73 extending therefrom with the area 75 behind the flexgrip fingers being solid and tubular. Antiseptic gel 77 is provided in the rear portion of tubular section 75. A bleeder hole 79 and O-ring 81 are also provided which perform the same function as the bleeder hole 56 and O-ring 58 previously discussed. Each finger 73 has a ramp projection 83 at the end thereof. Finally, portion 60 has a groove 85 formed about its periphery at a point behind the end of ball 64.

In operation, disposable section 60 is mounted to catheter 12, with needle 62 piercing seal 18, and the two are latched together with fingers 73 seating in groove 65 and being held therein by O-ring 67. While it might be possible to provide slots in housing 32, in particular in the grooves 63 and 65, so that disposable section 60 could be twisted and removed from seal 18, it is preferable that the disposable element 60 not be easily removable and that it be removable only by breaking fingers 73 using a suitable tool. This assures that a disposable section 60 will not be reused inadvertently and assures against inadvertent or intentional disconnection and reattachment by the patient or other unauthorized individuals. To the extent such removal and reattachment occur, the resulting damage to disposable section 60, and in particular the fingers 73 thereof, would be easily detectable by authorized medical personnel.

Each time the apparatus is to be used, needle 20 pierces seal 64. Needle 20 and seal 64 are also latched together in the manners previously described by having fingers 50 seat in groove 85. End cap 52 may be separated from element 60 by squeezing or rotatings fingers 50 in the manner previously described. Thus, assuming seal 64 also has a useful life of two hundred or more punctures, operating conservatively, and assuming four punctures a day, disposable section 60 might need to be replaced once every one to two months. Assuming seal 18 to have the same useful life, this would mean that seal 18 could be used for approximately ten years without difficulty and might be usable for much longer periods.

One problem with apparatus of the type shown in FIG. 1 is that the needle restricts the flow rate, preventing a desired flow rate from being achieved solely from gravity. The flow rate through needle 20, or needle 62, is inversely proportional to the length of the needle and increases as the diameter of the needle increases. This suggests that the needle utilized should be as short as possible. It also suggests that a relatively large gauge needle should be utilized; however, the use of a large gauge needle to achieve flow rate must be offset against the fact that a large gauge needle will make a larger hole in seal 18, making it more difficult for the seal to close after use, and adversely affecting the life of the seal. For most applications, adequate flow rates can be achieved through, for example, a 22-gauge needle by use of noninvasive pump 46, a 22-gauge needle being sufficiently small that seal 18 may easily reclose after use. The seal life figures used at various places have been based on the use of a 22-gauge needle. For a given gauge needle, a desired flow rate may be achieved by operating pump 46 at a sufficient rpm to create the pressure needed to achieve such flow. The discussion on flow rate also points up one potential problem with the tandem arrangement of FIG. 4 in that having two needles would have the same adverse effect on the flow rate as using a single needle which is twice as long. Since flow rate is inversely proportional to the needle length, the tandem arrangement further inhibits flow rate, forcing the use of a more powerful pump 46 or at least causing the pump to work harder. However it has been found that a small pump of 600 rpm capacity is powerful enough to provide pressure for fluid transfer even with a tanden arrangement.

As indicated above, when the tandem seal is utilized, the life of the seal 18 at the end of the catheter should be sufficiently long that it may never have to be replaced. Further, by the time the seal wears out, it may be desirable to surgically replace the catheter for other reasons.

Figure 5A:
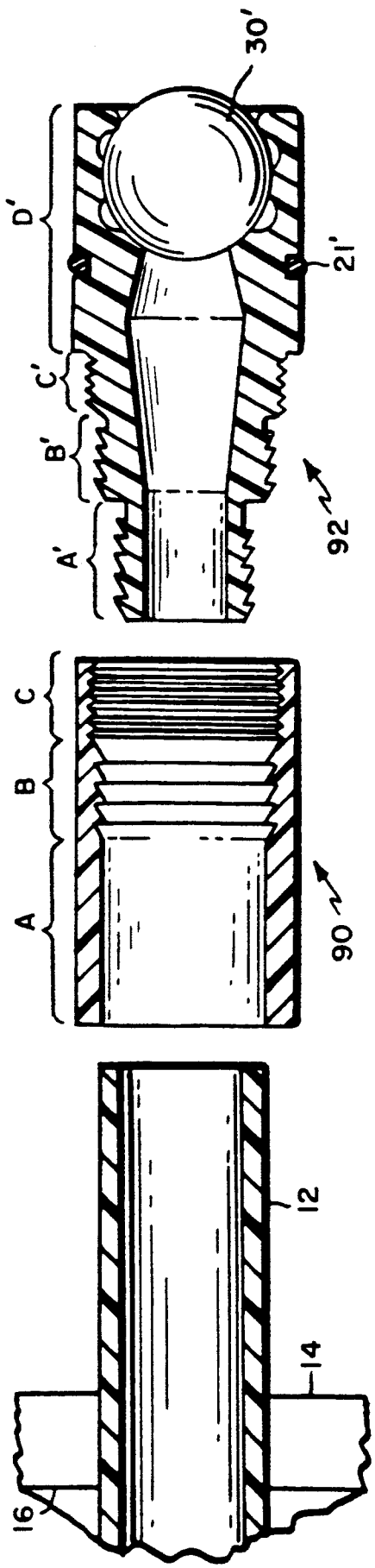
FIGS. 5A and 5B are cutaway side views of a replacement seal assembly for a catheter in exploded, unassembled condition and assembled condition respectively.
Figure 5B:
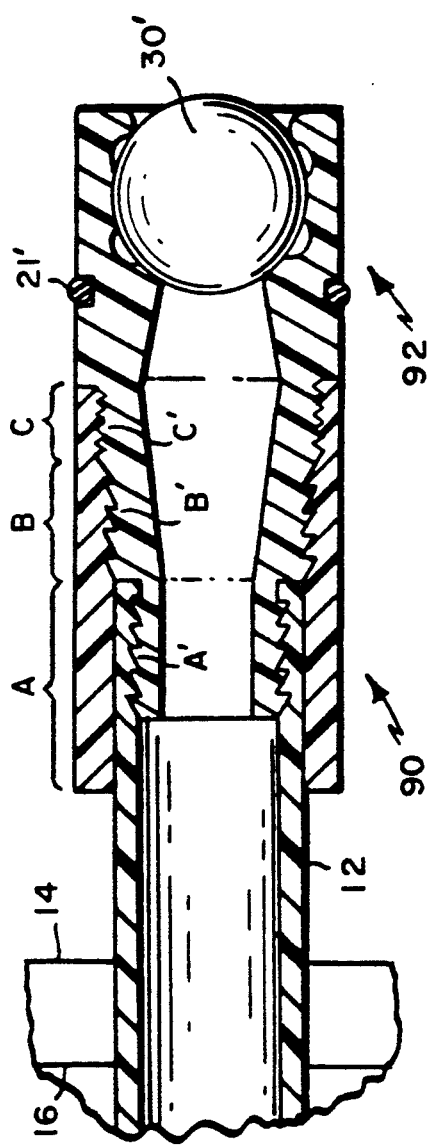
Figure 6A:
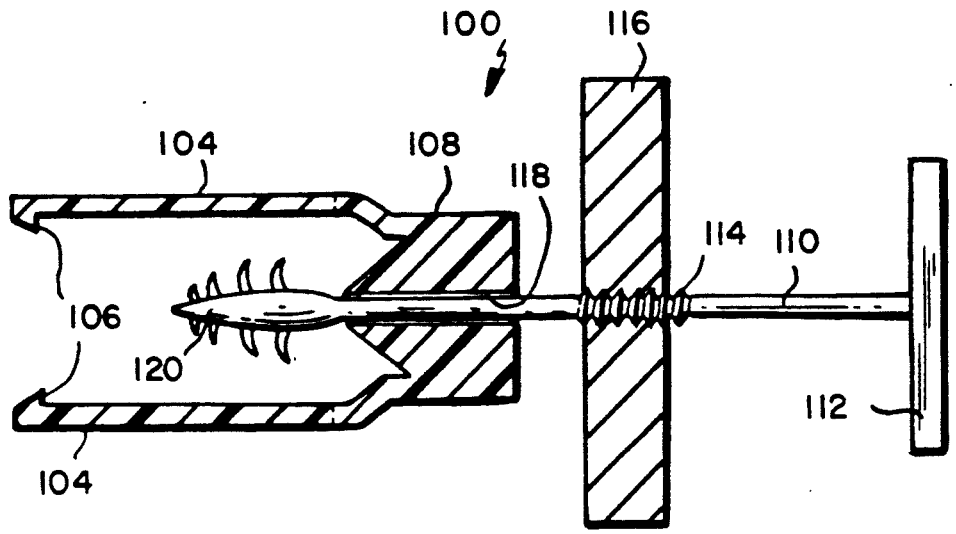
FIGS. 6A and 6B are a sealing ball extractor and a sealing ball replacement mechanism respectively for replacing the sealing ball in a catheter seal in accordance with the teachings of this invention.
Figure 6B:
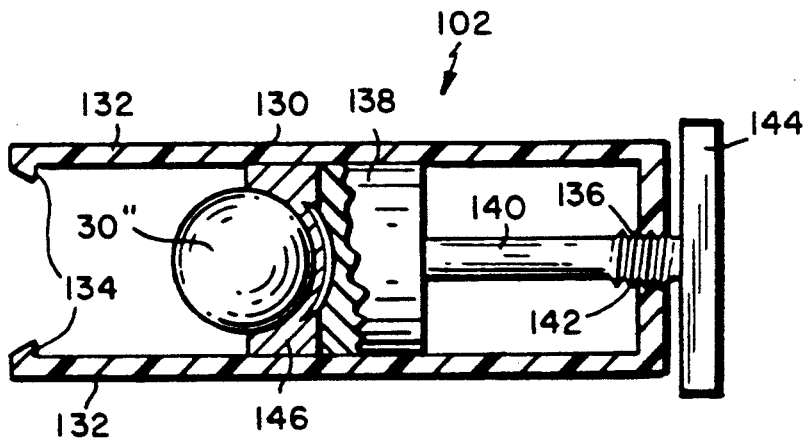

However, in some applications, it may be undesirable to use the tandem seal and/or the patient may be in treatment for a sufficient period of time that it will ultimately become necessary to replace the seal 18. While it is possible to screw mount or otherwise removably mount this seal to the catheter, to preserve the integrity of the seal and to avoid any possibility of infection, it is preferable that the seal not be removable by anyone other than trained medical personnel. This would normally require that special tools or equipment be required in order to remove the seal and to replace the seal. FIGS. 5A and 5B show one possible mechanism for removing and replacing the entire seal while FIGS. 6A and 6B show equipment for removing and replacing respectively only the ball portion of the seal.

Referring first to FIG. 5A, it is assumed that the seal has been cut off from the end of catheter 12. The replacement seal is in two parts, a cylindrical collar 90 and a replacement seal housing 92. Collar 90 has a smooth external surface and has an internal surface which is smooth along a section A which covers roughly the rear half of the collar, a relatively large toothed section B adjacent section A, and a much smaller toothed section C at the proximal end of the collar. The internal diameter of section A is such that this section may fit snugly over the end of the catheter 12.

Seal replacement housing 92 has a replacement silicon rubber ball 30' mounted at the proximal end thereof. A generally cylindrical chamber is formed behind ball 30'. The outer diameter of seal replacement housing 92 is roughly equal to that of collar 90 over an area D' extending from the proximal end to a point well behind the end of ball 30'. A small toothed section C' is provided having an outer diameter which roughly matches the inner diameter of section C of collar 90, a reduced outer diameter section B' is provided which is toothed to match the section B of collar 90 and has an outer diameter roughly matching the inner diameter of this section and a distal end A' of the seal replacement housing has a relatively large toothed outer diameter which is sized to be roughly the same as or slightly larger than the inner diameter of catheter 12. All of the teeth are angled as shown in FIG. 5A.

Referring to FIG. 5B, the elements are assembled by placing section A of collar 90 over the end of catheter 12. A suitable adhesive may be placed on the inner diameter of section A or on the outer surface of catheter 12 to hold collar 90 in place, but this should not be necessary. When collar 90 is in place, housing 92 is fitted into collar 90 until the teeth A engage the inside of catheter 12 and the teeth B'—B' and C'—C' engage. The housing 92 is then screwed and pushed into collar 90, the angles of the teeth permitting section A' of the housing to be moved into catheter 12 and the teeth B' and C' to be moved over the teeth B and C respectively. However, as may be seen in FIG. 5B, the angle of the teeth is such that, once these elements have been mated, movement in the opposite direction is not possible. Housing 92 is moved into collar 90 until it reaches the position shown in FIG. 5B where the proximal end of collar 90 butts against the distal end of section D of housing 92. When in this position, the end of catheter 12 is pinched between section A of collar 90 and A' of housing 92 with the teeth of section A' digging into the inside wall of the catheter and preventing the seal from being removed. A sealing ring 21' is provided on the outer surface of section D of housing 92 and serves the same function as the sealing ring 21 previously described. While grooves 63 and 65 and O-ring 67 are not shown in FIGS. 5A and 5B, if a latching seal is desired, these elements could be provided.

Referring to FIGS. 6A and 6B, a seal ball extraction tool 100 and a seal ball insertion or replacement tool 102 respectively are shown. The tool 100 has fingers 104 with ramp projections 106 at the ends thereof which function in the same way as the fingers 50 and ramp projections 61 to latch onto seal 18. Fingers 104 are formed at the end of a housing 108. A rod element 110 is provided which has a handle 112, a left-hand screw thread 114 near its center which passes through and mates with a corresponding screw thread in lever 116 and passes through a cylindrical channel 118 in the proximal end of housing 108, terminating in an enlarged screw thread 120 having a conical cross section.

In operation, once flexgrips 104 are engaged on seal 18, lever 116 is pressed against the proximal end of housing 108 and handle 112 is rotated to force screw thread 120 into the ball 30 to be removed. A suitable stop can be provided to prevent the screw thread from progressing through ball 30. Once screw thread 120 is fully embedded in ball 30, lever 116 is turned. The left-hand thread on this lever causes it to pull or apply force in the rearward or proximal direction on rod 110 drawing the rod, and the ball 30 secured on screw thread 120 in a rearward direction until the ball is extracted from the seal. The fingers 104 may then be released in the manner previously described and the tool 100 removed from the seal. Removed ball 30 may then be unscrewed from screw thread 120 and disposed of.

The seal replacement unit 102 shown in FIG. 6B is a disposable unit which is used only once. It includes a cylindrical housing 130 with flexgrip fingers 132 terminating in ramp projections 134 at its distal end and a screw threaded opening 136 at its proximal end. A plunger 138 is mounted to move in housing 130. Plunger 138 has a shaft 140 projecting from its rear end with a screw threaded portion 142 of the shaft passing through threaded opening 136 in the housing. Shaft 140 terminates at its proximal end in a handle 144. Replacement ball 30" is held against plunger 138 by an antiseptic gel 140. In operation, flexgrip legs 32 are mounted on seal 18 latching with grooves 63 or 65 in the manner previously described. Handle 44 is then rotated pressing plunger 138 against ball 30" until the ball has been pressed into the socket in housing 32. Once a new ball has been inserted in the socket, the unit 132 is removed by releasing the flexgrip fingers 132 in one of the manners previously described and unit 132 is disposed of.

While for the preferred embodiment, the apparatus is being utilized for peritoneal dialysis, with dialysate being initially pumped from receptacle 44 through tube 40, needle 20, and catheter 12 into the patient's peritoneal cavity, and pump 46 then being reversed to cause dialysate saturated with bodily waste to be pumped from the peritoneal cavity through catheter 12, needle 20, and tube 40 into receptacle 44, it should be apparent that the technique of this invention can be utilized in a variety of other applications where fluid is to be pumped into or extracted from a particular body area. For example, this technique could be utilized to simplify the use of implanted catheters for cancer patients undergoing chemotherapy and might also be utilized with I.C.U. patients needing to receive a variety of IV's over extended periods, hemophiliacs requiring frequent blood transfusions, diabetics requiring frequent insulin injections, and the like.

Further, while particular seals have been shown for the preferred embodiment, it is apparent that other techniques for sealing the end of the catheter, either currently existing or developed in the future, may be utilized in place of the seals 18 shown in FIGS. 2 and 3. Other techniques than those disclosed might also be utilized to releasably secure the line 40 from the pump to either seal 18 or replaceable element 60, to more permanently secure seal 18 to element 60 and/or to replace seal 18 or ball portions 30 thereof. Noninvasive pump 46 may also be replaced by suitable means for driving the fluid through needle 20 which, in the simplest case, may be a hand operated device.

Thus, while the invention has been particularly shown and described above with reference to preferred embodiments, the foregoing and other changes in form and detail may be made therein by one skilled in the art without departing from the spirit and scope of the invention.

What is claimed is:

1. Apparatus for transferring a selected fluid in a desired direction to or from a selected body area of a medical PATENT, the apparatus comprising:
a catheter having a distal end and a proximal end, the length of the catheter between said ends being sufficiently greater than the distance from said selected body area where said distal end is adapted to be implanted to an exit point for the catheter from the patient's body, that a length of the catheter may extend external to the patient's body when the catheter is fully implanted;
means located at the proximal end of the catheter for sealing said catheter proximal end, said sealing means including a sealing element of a material which may be repeatedly punctured by a needle and which reseals when the needle is removed;
receptacle means adapted to function as a source or sink for said selected fluid;
a needle adapted to puncture sd sealing element;
a tubular means connecting said receptacle means and said needle; and
noninvasive pump means for pumping the selected fluid in the desired direction at a desired flow rate between said body area and said receptacle means through said catheter, needles, and tubular means.

2. An apparatus as claimed in claim 1 wherein said sealing means may be removed from said catheter, and including means for replacing the removed seal.

3. An apparatus as claimed in claim 2 wherein said sealing means is removed by cutting it off the end of the catheter, and wherein said means for replacing includes means for securing a replacement seal to the catheter end.

4. An apparatus as claimed in claim 3 wherein said means for replacing includes collar means adapted to fit over the cut end of the catheter, and a replacement seal means containing a replacement sealing element, said replacement seal means having a toothed distal end which fits inside the cut end of the catheter to, in conjunction with the collar means, grasp the end of the catheter therebetween, and which has an external surface which mates with internal surfaces of the collar means to secure the collar means and the replacement sealing means together.

5. An apparatus as claimed in claim 1 including means operative when the needle is piercing the sealing means for inhibiting relative movement between the needle and sealing means in both a direction substantially parallel to the needle and in directions perpendicular thereto.

6. An apparatus as claimed in claim 5 wherein said inhibiting means includes means for releasably latching the needle and sealing means together.

7. An apparatus as claimed in claim 1 including a disposable section having a housing with a second needle mounted near one end and a second puncturable sealing element at the other end, the disposable section being adapted for use between the needle and sealing means to enhance the life of the sealing element.

8. An apparatus as claimed in claim 7 including means for latching said sealing means and said disposable sections.

9. An apparatus as claimed in claim 8 wherein said latching means permits the sealing means and disposable section to be separated only by breaking the disposable sections.

10. A method for transferring a selected fluid in a desired direction to or from a selected body area of a medical patient, the method comprising the steps of:
- surgically implanting the distal end of a catheter in said body area;
- providing a length of said catheter, which length of catheter extends through the patient's body to a body exit point, and extends for a selected length beyond said exit point, terminating in the proximal end of the catheter, which end is spaced from the exit point;
- sealing said proximal end of the catheter with a seal which includes a sealing element of a material which may be repeatedly punctured by a needle and which reseals when the needle is removed;
- puncturing said sealing element with a needle which is connected through a tubular means to a receptacle means adapted to function as a source or sink for said selected fluid; and
- noninvasively pumping the selected fluid int he desired direction between said body area and said receptacle means through said catheter, needle and tubular means.

11. A method as claimed in claim 10 including the step of removing said seal from said catheter and replacing the removed seal with a new seal, said removing and replacing step including the steps of pinching off the catheter to close it, removing the seal from the external proximal end of the catheter, affixing the new seal to said proximal end, and opening the catheter.

12. A method as claimed in claim 10 including the steps of inhibiting relative movement between the needle and seal when the needle is piercing the seal, and removable latching said needle and seal.

13. A method as claimed in claim 10 including the step of mounting a disposable section having a housing with a second needle mounted near one end and a second puncturable sealing element at the other end, between the needle and seal to enhance the life of the sealing element.

14. A method as claimed in claim 13 wherein said mounting step includes the steps of puncturing said sealing element with said second needle, and puncturing said second sealing element with said needle, said disposable section remaining mounted to the catheter and seal during multiple punctures.

15. A method as claimed in claim 10 wherein said method is being used in peritoneal dialysis, wherein said selected body area is the peritoneal area, and wherein said selected fluid is dialysate, clean dialysate being initially provided from said receptacle means and dialysate saturated with waste products being removed by the method to the receptacle means.

* * * * *